(12) United States Patent
Bush, Jr. et al.

(10) Patent No.: US 6,936,032 B1
(45) Date of Patent: Aug. 30, 2005

(54) MEDICATION DELIVERY PEN

(75) Inventors: Charles L. Bush, Jr., Fairfield, NJ (US); Douglas Paddock, Hardyston, NJ (US); John E. Burbank, III, Ridgefield, CT (US); Jonathan B. Gabel, Randolph, NJ (US); Amir Ali Sharifi-Mehr, Bloomingdale, NJ (US); Tuan V. Nguyen, Hillsborough, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/049,655

(22) PCT Filed: Jul. 31, 2000

(86) PCT No.: PCT/US00/20938

§ 371 (c)(1),
(2), (4) Date: Oct. 15, 2002

(87) PCT Pub. No.: WO01/10484

PCT Pub. Date: Feb. 15, 2001

Related U.S. Application Data

(60) Provisional application No. 60/147,330, filed on Aug. 5, 1999.

(51) Int. Cl.$^7$ .............................................. A61M 5/00
(52) U.S. Cl. ..................................................... 604/187
(58) Field of Search ............................... 604/181, 186, 604/187, 188, 192, 221, 232, 218, 224, 234; 222/46–48, 222/309

(56) References Cited

U.S. PATENT DOCUMENTS 4,858,607 A * 8/1989 Jordan et al. ................ 606/182
5,688,251 A * 11/1997 Chanoch ...................... 604/208

* cited by examiner

*Primary Examiner*—Kevin C. Simmons
(74) *Attorney, Agent, or Firm*—Alan W. Fiedler

(57) ABSTRACT

A medication delivery pen having a magnifier, a spring biased leadscrew and a mechanism to allow the user to easily reset the dose on the medication delivery pen if the user requires a smaller dose than has been set.

4 Claims, 8 Drawing Sheets

MEDICATION DELIVERY PEN

This application claims the benefit of provisional application No. 60/147,330 filed Aug. 5, 1999.

BACKGROUND OF THE INVENTION

1. Field of the Invention

The present invention relates to a medication delivery pen having a variety of features and, more particularly, a medication delivery pen having a spring biased leadscrew to make priming easier and minimize underdosing and a magnifier for setting the dose.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of the day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen includes a cartridge holder into which a cartridge of insulin or other medication may be received. The cartridge holder is an elongate generally tubular structure with proximal and distal ends. The distal end of the prior art cartridge holder includes mounting means for engaging a double-ended needle cannula. The proximal end also includes mounting means for engaging a driver and dose setting apparatus as explained further below. A disposable cartridge for use with the prior art cartridge holder includes a distal end having a pierceable elastomeric seal that can be pierced by one end of a double-ended needle cannula. The proximal end of this prior art cartridge includes a plunger slidably disposed in fluid tight engagement with the cylindrical wall of the cartridge. This prior art medication delivery pen is used by inserting the cartridge of medication into the cartridge holder. A prior art pen body then is connected to the proximal end of the cartridge holder. The pen body includes a dose setting apparatus for designating a dose of medication to be delivered by the pen and a driving apparatus for urging the plunger of the cartridge distally for a distance corresponding to the selected dose.

The user of the pen mounts a prior art double-ended needle cannula to the distal end of the cartridge holder such that the proximal point of the needle cannula pierces the elastomeric seal on the cartridge. The patient then selects a dose and operates the pen to urge the plunger distally to deliver the selected dose. The dose selecting apparatus returns to zero upon injection of the selected dose with this prior art medication delivery pen. The patient then removes and discards the needle cannula, and keeps the prior art medication delivery pen in a convenient location for the next required medication administration. The medication in the cartridge will become exhausted after several such administrations of medication. The patient then separates the cartridge holder from the pen body. The empty cartridge may then be removed and discarded. A new cartridge can be inserted into the cartridge holder, and the cartridge holder and pen body can be reassembled and used as explained above.

The above described medication delivery pen is effective and much more convenient for self-administration of medication than the hypodermic syringes that use separate medication cartridges. However, the above-described medication delivery pen requires a number of parts which make the manufacture of these pens very expensive. Hence, it is necessary to provide a medication delivery pen having a simple mechanism for setting the desired dose, simplifies loading of the cartridge, and makes priming easier to minimize underdosing.

SUMMARY OF THE INVENTION

The present invention relates to a medication delivery pen that addresses the above-identified problems and provides numerous features that have become expected by medication delivery pen users.

The medication delivery pen according to the present invention includes a mechanism that automatically disengages the drive mechanism from the dose control mechanism to permit the user to reset the dose on the medication delivery pen.

Another feature of the present invention is an automatic mechanism that allows the user to easily load a new cartridge and automatically repositions the leadscrew next to the plunger when the cartridge holder is mounted on the body of the medication delivery pen.

Another feature of the present invention is a magnifier for easy viewing and setting of the desired dose.

DETAILED DESCRIPTION OF THE INVENTION

Figure 1:
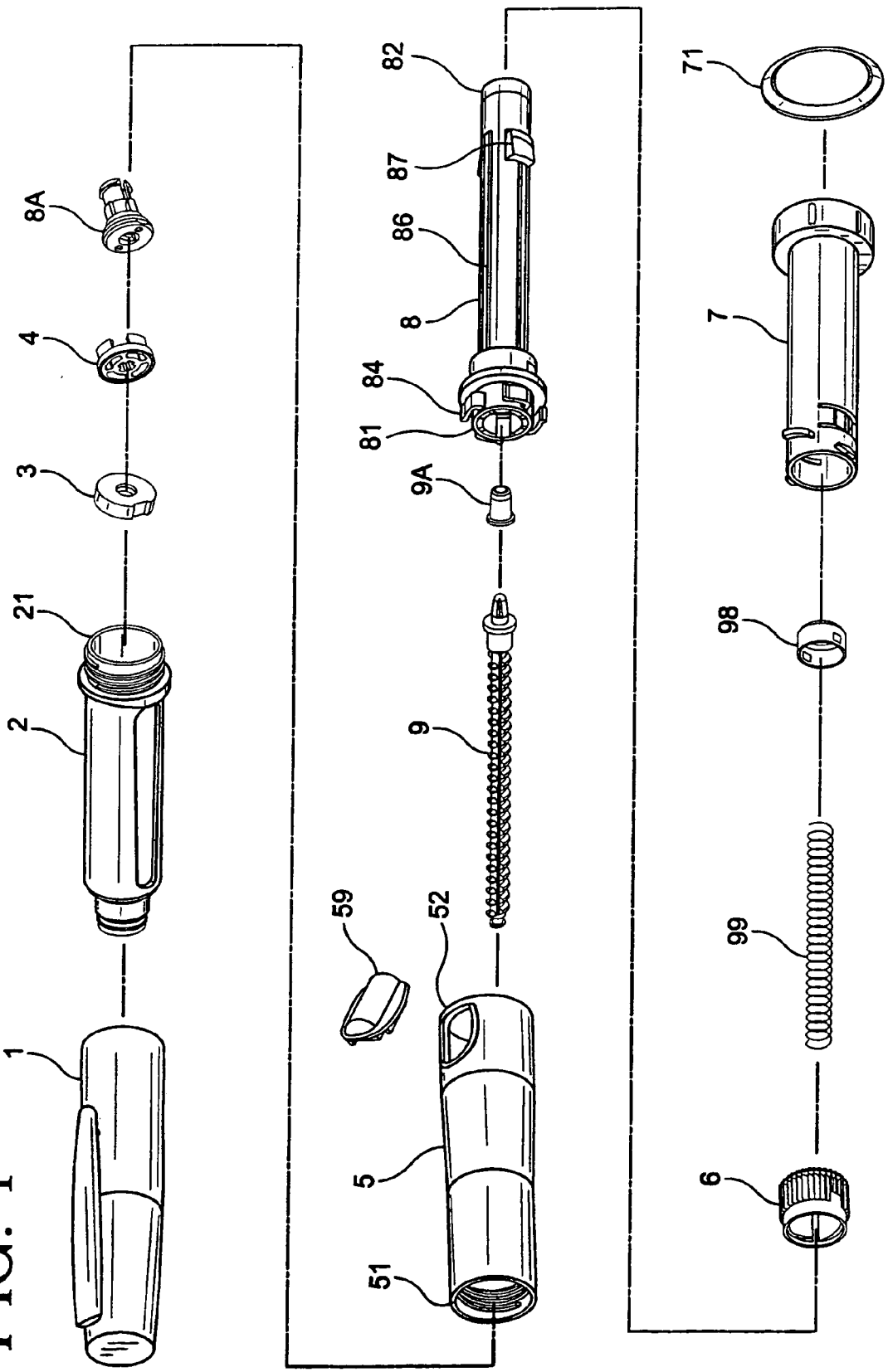
FIG. 1 is an exploded perspective view of a medication delivery pen according to the present invention.

A medication delivery pen 10 according to the present invention is shown in FIGS. 1–12. Medication delivery pen 10 includes a cap 1 removably attached to a cartridge holder 2 so to cover cartridge holder 2 between uses of medication delivery pen 10. Cartridge holder 2 receives a cartridge 100, shown in FIG. 9, that is commonly used in such medication delivery pens to provide medication and/or insulin for an injection. Medication delivery pen 10 includes a body 5 having a distal end 51 and a proximal end 52, with cartridge holder 2 being attached to distal end 51 of body 5. Medication delivery pen 10 also includes a dose knob 7, a driver 8, a leadscrew 9, a leadscrew spinner 3, a retract nut 4, a shuttle 6, and a push button 71. Each of these elements are more clearly shown in FIGS. 2–8 and are more fully described below.

Driver 8 includes a distal end 81 and a proximal end 82, wherein distal end 81 receives drive nut 8A. In addition, driver 8 includes a plurality of ratchet fingers 84 at distal end 81 that engage a ratchet 53, shown in FIG. 6, within body 5 to allow driver 8 to rotate only in one direction with respect to body 5. Drive nut 8A, shown in FIG. 3, includes a set of threads 85 that interface with a matching set of threads 93 on leadscrew 9, shown in FIG. 2. Leadscrew 9 shown in FIG. 2 includes a distal end 91 and a proximal end 92, with proximal end 92 receiving an end cap or co-pilot 9A, shown in FIG. 1, and distal end 91 receiving leadscrew spinner 3 also shown in FIG. 1. FIG. 2 shows a distinctive thread formed by a set of threads 93 on leadscrew 9. Each thread 93 includes distinctive pyramid projection 94 formed by grooves 95 that cut through threads 93 in a longitudinal direction on leadscrew 9.

Figure 3:
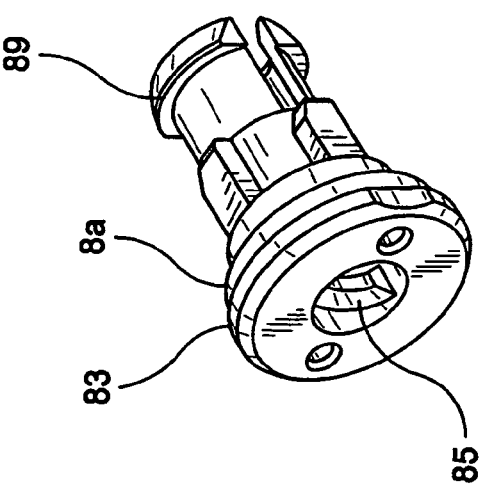
FIG. 3 is a perspective view of the drive nut shown in FIG. 1.

FIG. 3 shows drive nut 8A which is received in distal end 81 of driver 8. Drive nut 8A is held within distal end 81 of driver 8 by flanges 89 on drive nut 8A. During assembly, drive nut 8A is inserted through distal end 51 of body 5 while driver 8 is inserted through the proximal end 52 of body 5 and snapped together within body 5 to capture a wall 57 within body 5, shown in FIG. 6.

Figure 4:
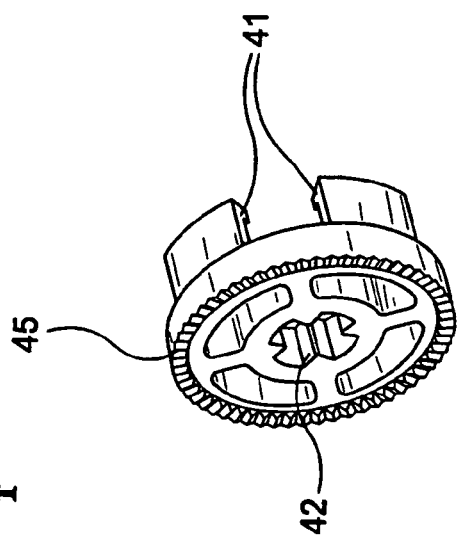
FIG. 4 is a perspective view of the retract nut shown in FIG. 1.

FIG. 4 is a perspective view of retract nut 4 that more clearly shows attachment arms 41 that mate with snap ring 83 on drive nut 8A to rotatably attach retract nut 4. Retract nut 4 also includes an opening 42 therethrough having a plus sign shape that mates with a set of grooves 94 in leadscrew 9, shown in FIG. 2, to prevent leadscrew 9 from rotating with respect to retract nut 4. Retract nut 4 also has a distal toothed surface 45 that mates with teeth 21 on cartridge holder 2 to prevent retract nut 4 and leadscrew 9 from rotating when cartridge holder 2 is mounted on body 5. However, when cartridge holder 2 is not mounted into body 5, retract nut 4 and leadscrew 9 are free to rotate which permits leadscrew 9 to be free to backdrive into body 5 as the user pushes a new cartridge into place. A leadscrew spinner 3 is attached to a distal end 91 of leadscrew 9 and is allowed to spin freely on leadscrew 9, shown in FIG. 2, in relation to a rubber plunger 111 within the cartridge as leadscrew 9 is backdriven into body 5.

Figure 2:
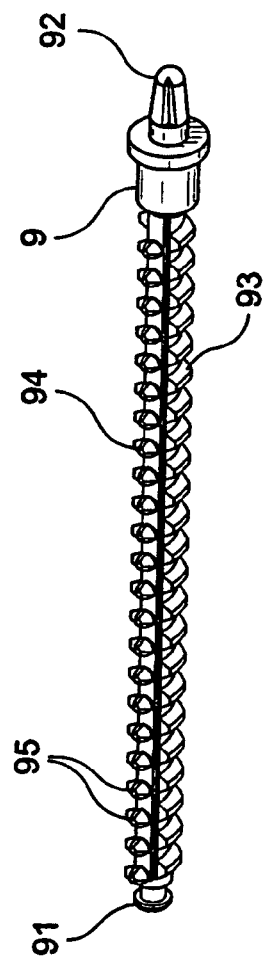
FIG. 2 is a perspective view of the leadscrew in the medication delivery pen shown in FIG. 1.

Medication delivery pen 10 according to the present invention also includes a spring 99 and a spring cap 98, as shown in FIG. 1. During assembly spring 99 is placed into driver 8 and is held within driver 8 using spring cap 98 that attaches to proximal end 82 of driver 8. Spring 99 is then contained between spring cap 98 and end cap 9A to bias leadscrew in the distal direction to reduce priming of leadscrew 9 with rubber plunger 111 and make priming much easier than conventional pens. End cap or co-pilot 9A aids in guiding spring 99 during backdriving to reduce friction or rotation of spring 99. Spring 99, however, is not used to drive leadscrew 9 during medication injection.

When cartridge holder 2 mates with retract nut 4, leadscrew 9 is locked against rotation which then enables threads 85 within drive nut 8A to drive leadscrew 9 in the distal direction towards and against the rubber plunger 111 within cartridge 100 during a dispensing operation. Snap ring 83 on drive nut 8A also allows retract nut 4 to float captive thereon thus trapping it from spinning down leadscrew 9 when exchanging cartridges, should a user invert medication delivery pen 10 when changing cartridges.

Figure 5:
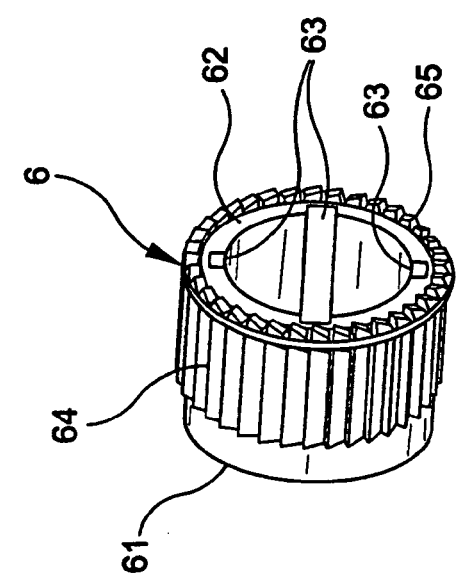
FIG. 5 is a perspective view of the shuttle shown in FIG. 1.

FIG. 5 is a perspective view of shuttle 6 showing a plurality of keyways 63 therein that travel within a respective set of keys 86 on driver 8, shown in FIG. 1. Shuttle 6 also includes a distal end 61 and a proximal end 62, proximal end 62 having a plurality of teeth 65 and a plurality of ratchets 64 extending from teeth 65 towards distal end 61. Ratchets 64 engage with a plurality of ratchet fingers 73 on a distal end 71 of dose knob 7, shown in FIG. 7 and discussed further below.

Figure 6:
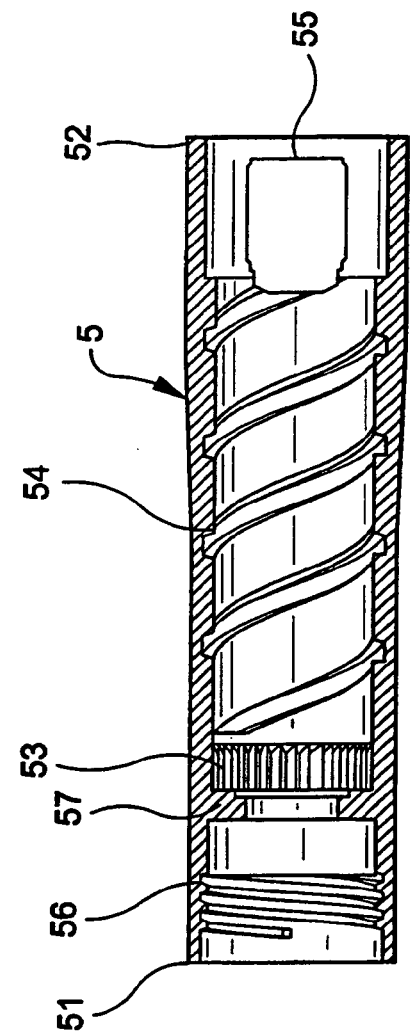
FIG. 6 is a cross-sectional view of the body of the medication delivery pen shown in FIG. 1.

FIG. 6 is a cross-sectional view of body 5 more clearly showing distal end 51 and proximal end 52 having a set of dose setting threads 54 therein together with a dose viewing window 55 that receives a magnifier 59 used to magnify the dosage numerals 74 on dose knob 7. Another set of threads 56 located within distal end 51 are used to attach cartridge holder 2 in this embodiment. Of course, other means for attaching cartridge holder 2 to body 5 could also be used and fall within the scope of the present invention as long as sufficient force is applied to retract nut 4 to prevent rotation of retract nut 4 and leadscrew 9 within body 5 when cartridge holder 2 is attached to body 5.

Figure 9:
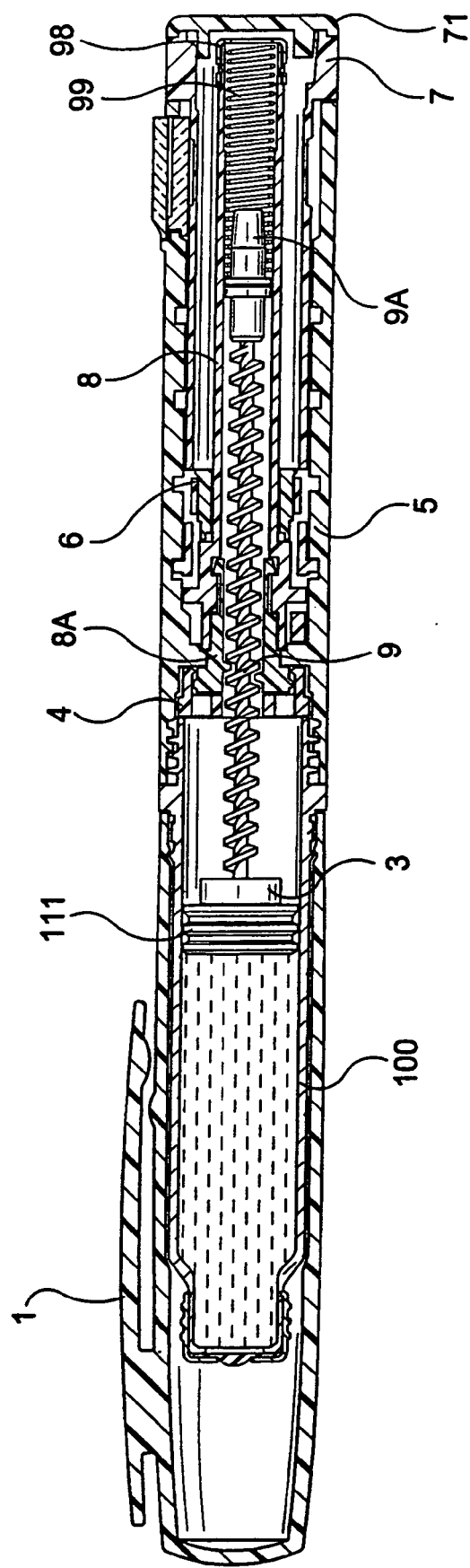
FIG. 9 is a cross-sectional view of the medication delivery pen shown in FIG. 1 fully assembled and in a dose setting condition.

FIG. 9 is a cross sectional view of medication delivery pen 10 shown in FIG. 1 fully assembled and in a dose setting condition or a condition for transportability. In FIG. 9 shuttle 6 is fully received within dose knob 7 such that teeth 65 on proximal end 62 of shuttle 6 are engaged with teeth 78, shown in FIG. 8, within dose knob 7. This causes shuttle 6 and dose knob 7 to rotate together during dose delivery.

Figure 7:
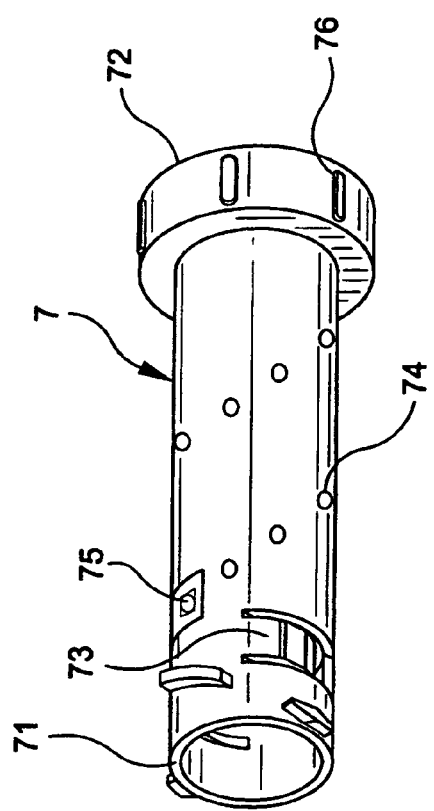
FIG. 7 is a perspective view of the dose knob of the medication delivery pen shown in FIG. 1.
Figure 8:
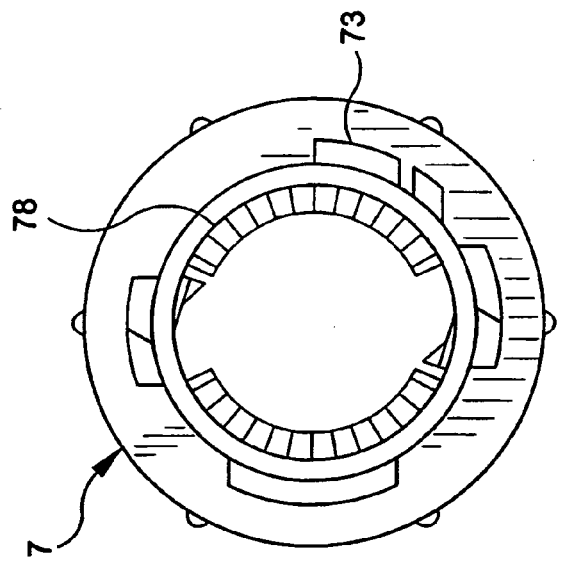
FIG. 8 is a distal end view of the dose knob of the medication delivery pen shown in FIG. 1.

FIG. 7 is a perspective view of dose knob 7 having a distal end 71 and a proximal end 72, with a textured section 76 near proximal end 72 to aide the user in turning dose knob 7 to set a desired dose when using medication delivery pen

Figure 10:
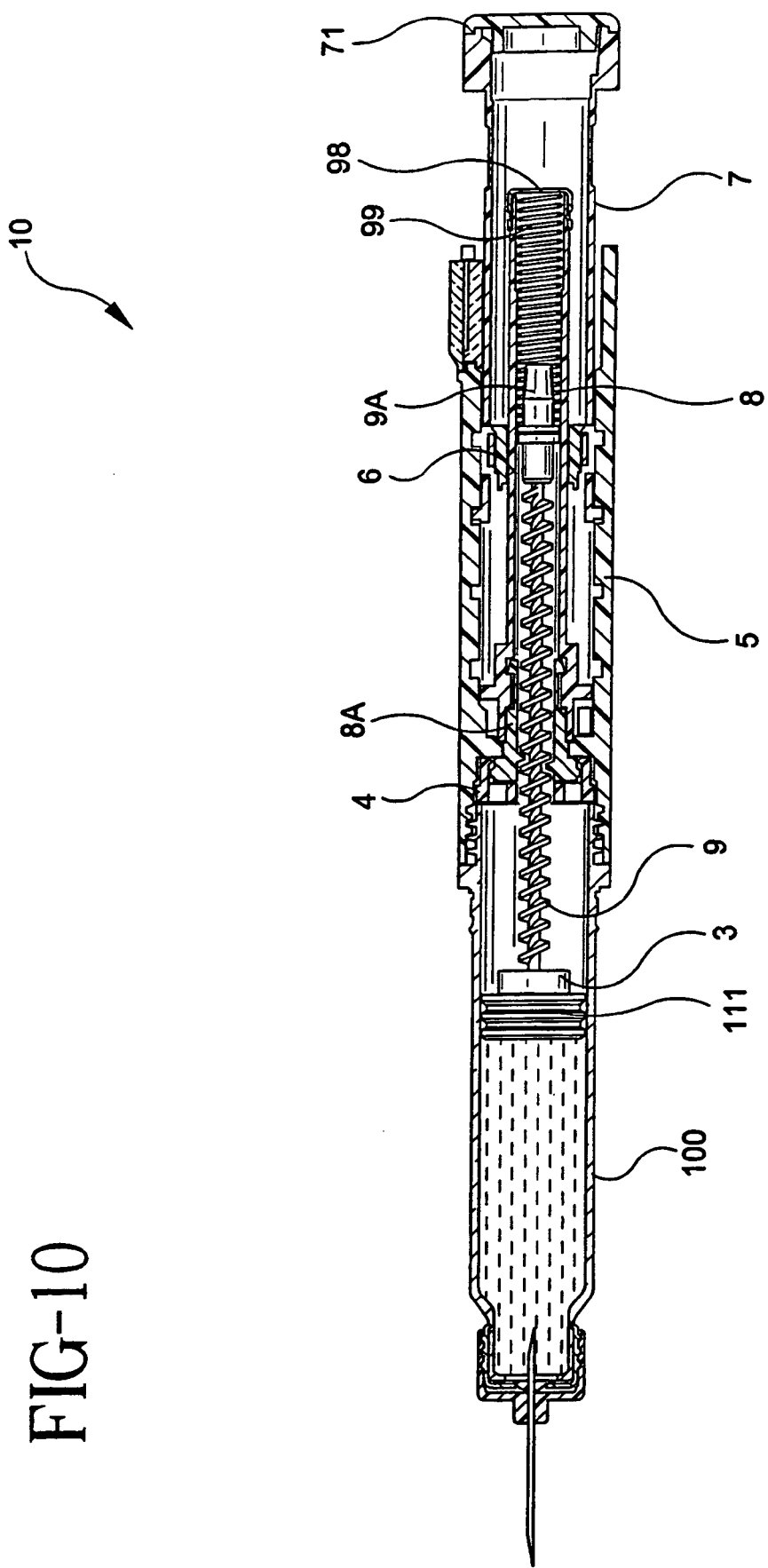
FIG. 10 is a cross-sectional view of the medication delivery pen shown in FIG. 9 in a dose set condition.
Figure 11:
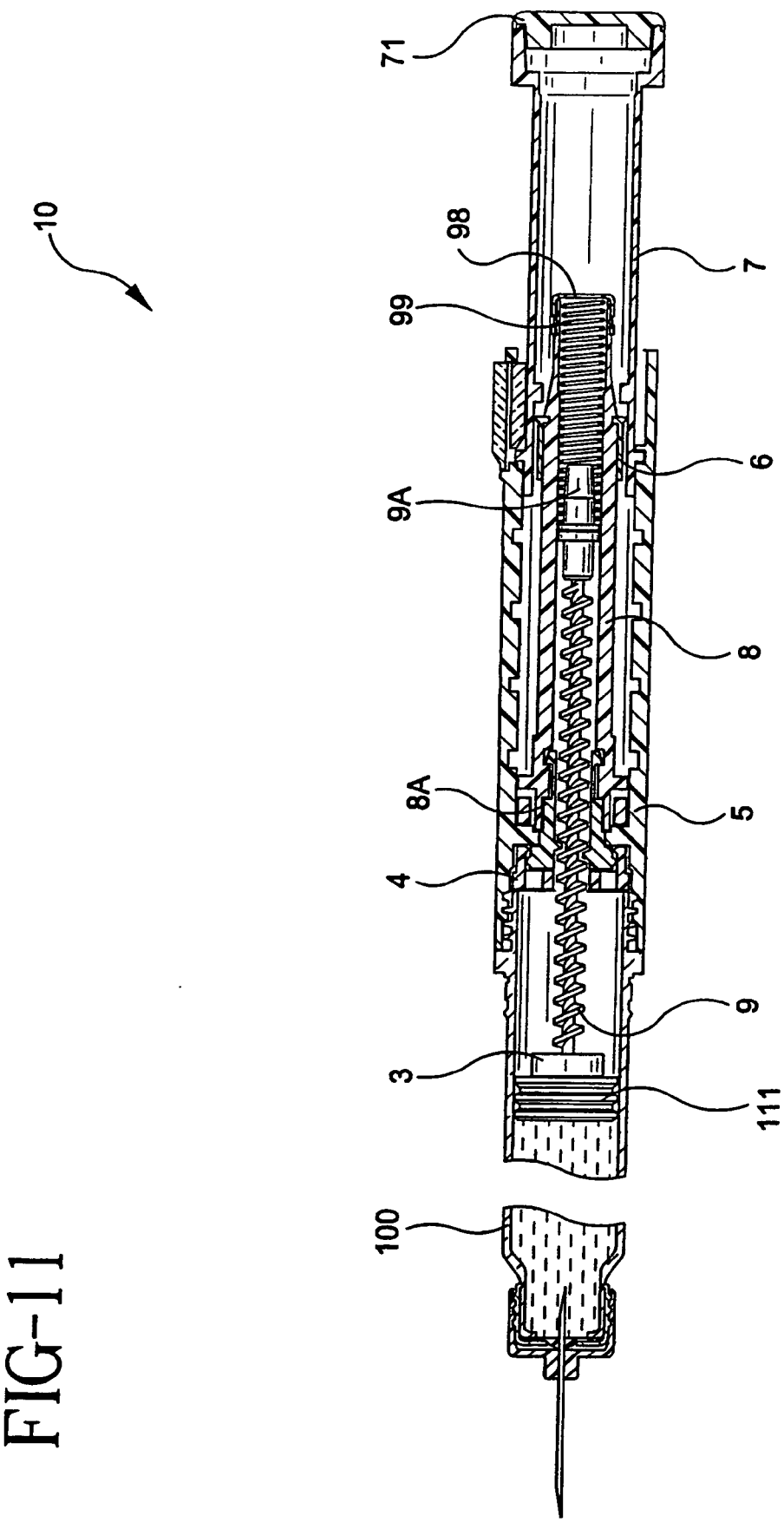
FIG. 11 is a cross-sectional view of the medication delivery pen shown in FIG. 9 in a reset dose condition.
Figure 12:
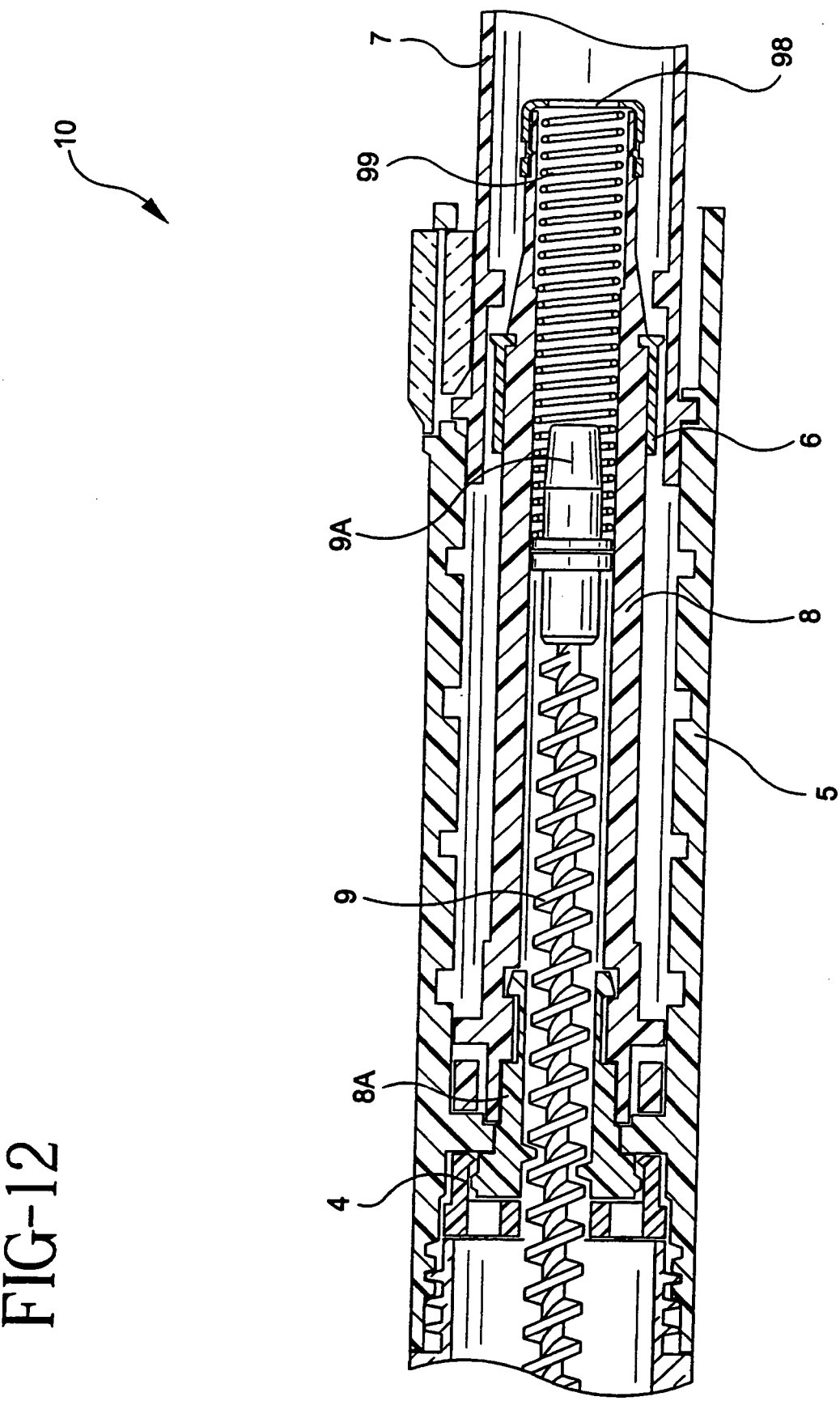
FIG. 12 is an enlarged cross-sectional view of a section of the medication delivery pen shown in FIG. 11.

10. Distal end 71 includes the plurality of ratchet fingers 73 that engage ratchet 64 on shuttle 6 when setting a dose, as shown in FIG. 10, until medication delivery pen 10 is in a reset condition, as shown in FIG. 11. When medication delivery pen 10 is in the reset condition, shuttle 6 has disengaged from dose knob 7 as clearly seen in FIGS. 11 and 12. Alternatively, as shown in FIG. 10 during a dose setting condition, shuttle 6 is within dose knob 7 such that ratchet 64 is engaged with ratchet fingers 73. When a user is turning dose knob 7, shuttle 6 slides along driver 8 towards proximal end 52 of body 5 and dose knob 7 rotates around shuttle 6 causing ratchet fingers 73 on dose knob 7 to engage and disengage with ratchet 64 on shuttle 6 to provide an audible and tactile signal during dose setting. As shuttle 6 slides along driver 8, keyways 63 within shuttle 6 interact with keys 86 on driver 8. After a desired dose has been set by the user using dose knob 7, movement of dose knob 7 in a distal direction will cause shuttle 6 to rotate due to the interaction between teeth 65 on proximal end 62 of shuttle 6 and teeth 78 within dose knob 7. As shuttle 6 rotates, keyways 63 within shuttle 6 interact with keys 86 on driver 8 to rotate drive nut 8A about leadscrew 9 and move leadscrew 9 in a distal direction to dispense medication from cartridge 100.

The user sets a desired dose by rotating dose knob 7 in a clockwise direction until the desired dose is displayed through magnifier 59 in body 5. Dose knob 7 includes a plurality of dosage numerals 74 that show through window 55 and an indicator 75, i.e., ▲, that identifies a "reset condition" for medication delivery pen 10. When the desired dose is reached, the user depresses a push button 71 attached to proximal end 72 of dose knob 7 until dose knob 7 has fully returned within body 5 to the dose setting position shown in FIG. 9.

A significant function of the drive mechanism within medication delivery pen 10 is that if the user overshoots the desired dose, medication delivery pen 10 can be reset so that the user may redial for the desired dose. This is accomplished by rotating dose knob 7 completely past the maximum value (30 or 60) until indicator 75 on dose knob 7 is displayed in through magnifier 59 within body 5. This disengages ratchet fingers 73 within dose knob 7 from ratchet 64 on shuttle 6 by forcing them apart and releasing shuttle 6 from within dose knob 7. This action is caused by proximal end 62 engaging with a set of stops 87, shown in FIG. 1, on driver 8. Dose knob 7 is then free to rotate back to an initial dose position ("0") upon which ratchet fingers 73 are forced to reengage with ratchet 64 on shuttle 6. Disengaging and re-engaging ratchet 64 and ratchet fingers 73 requires significant tactile manipulation and results in an audible click which alerts the user that the resetting function has been performed. After performing the resetting function, ratchet 64 and ratchet fingers 73 are no longer engaged so that no audible or tactile feedback is generated during rotation of dose knob 7 until reset function is completed.

While the present invention has been described with respect to a preferred embodiment, it is apparent that various changes can be made without departing from the scope of the invention as defined by the appended claims.

What is claimed is:

1. A medication delivery pen comprising:
    a body having opposing proximal and distal ends;
    a dose control mechanism disposed in the proximal end of the body for setting and administering a dosage of medication;
    a cartridge holder having a cartridge with a pierceably sealed distal end, an open proximal end removably attachable to the distal end of the body, and a plunger in sliding, fluid tight engagement within said cartridge;
    a drive mechanism coupled between the dose control mechanism and the cartridge to exert an axial force on the plunger to inject the set dosage of medication, wherein the dose control mechanism triggers the drive mechanism to administer the injection of medication held in the cartridge; and
    a mechanism that automatically disengages the drive mechanism from the dose control mechanism when the dose control mechanism is rotated past a maximum value to a predetermined position, such that the dose control mechanism is free to rotate back to an initial dose position where the drive mechanism and dose control mechanism are then re-engaged to permit the user to set a new dosage on the medication delivery pen,
    wherein the mechanism for automatically disengaging the drive mechanism from the dose control mechanism comprises a plurality of stops on the drive mechanism that interact with the dose control mechanism when the dose control mechanism is at the predetermined position to disengage ratchet fingers on the dose control mechanism from a ratchet on the drive mechanism.

2. The medication delivery pen of claim 1, further comprising a magnifier on the body for viewing and setting of the desired dosage using the dose control mechanism.

3. The medication delivery pen of claim 1, wherein the predetermined position identifies a reset condition for the medication delivery pen.

4. The medication delivery pen of claim 1, wherein an indicator on the dose control mechanism identifies the predetermined position.

* * * * *